United States Patent
Stewart (10) Patent No.: US 6,604,092 B1
(45) Date of Patent: Aug. 5, 2003

(54) EXPERT SYSTEM UTILIZING A KNOWLEDGE BASE AND DESIGN OF EXPERIMENT (DOE) TECHNIQUES

(75) Inventor: Lisa Ellen Stewart, Berkeley, CA (US)

(73) Assignee: Lisa E. Stewart (*) Notice: Subject to any disclaimer, the term of this patent is extended or adjusted under 35 U.S.C. 154(b) by 0 days.

(21) Appl. No.: 09/258,493

(22) Filed: Feb. 26, 1999

(51) Int. Cl.[7] .............................................. G06F 17/00
(52) U.S. Cl. ............................................ 706/47; 703/2
(58) Field of Search ............................. 706/47; 716/18; 703/2; 717/1; 358/1.15, 438, 440, 402; 709/224; 702/82

(56) References Cited

U.S. PATENT DOCUMENTS

| | | | |
|---|---|---|---|
| 4,472,770 A | 9/1984 | Li | 700/47 |
| 4,710,864 A | 12/1987 | Li | 700/47 |
| 4,910,660 A | 3/1990 | Li | 700/47 |
| 5,107,499 A | 4/1992 | Lirov | 714/26 |
| 5,253,331 A | 10/1993 | Lorenzen et al. | 706/45 |
| 5,493,729 A | 2/1996 | Nigawara et al. | 706/52 |
| 5,842,193 A | * 11/1998 | Reilly | 706/45 |
| 6,148,277 A | * 11/2000 | Asava et al. | 703/22 |

FOREIGN PATENT DOCUMENTS

JP  5-7200662  8/1995

OTHER PUBLICATIONS

Reference Data for Radio Engineers, 6th Edition, 1968, Howard W. Sams and Company Inc., Chapter 3.*
Ronald Caulcutt, "Statistics in Research and Development", Second Edition, Chapman & Hall, 1991, pp 339–449, London*New York.
B.D. Cobb, and J.M. Clarkson, "A Simple Procedure for Optimizing the Polymerase Chain Reaction (PCR) Using Modified Taguchi Methods," Nucleic Acids Research, 1994, vol. 22, No. 18, pp. 3801–3805.
P. Brions, "Experimental Design: A useful Tool for PCR Optimization", BioTechniques, Jul. 1996, 21:134–140.
Charles G. Pfeifer, "Why Don't More Researchers Use Design of Experiments?", R&D Magazine, Jan. 1995, pp. 31.
Robert Kolp, Jr., "DOE Makes Research Pay Off", R&D Magazine, Apr. 1997, pp. 43.
Matsoft, Inc., "S+DOX: Technical Overview", MathSoft., Inc., 1994, pp 3–18, Seattle, WA.
P.D. Haaland and D. Write, "Experimental Design Software Improves the Efficiency of Product Development", Scientific Computing & Automation, Mar. 1995.
Holle & Huttner GmbH, "Cycle Manager"[Software], http://www.h–net.com/h–net98/86–e.htm.

* cited by examiner

Primary Examiner—John A. Follansbee
Assistant Examiner—Joseph P. Hirl (57) ABSTRACT

This invention teaches the user with a design and tool for protocols. It integrates the advantages of a user interface with a simple set of steps, powerful statistical methods, flexible and specialized knowledge bases which can incorporate previously optimized protocol methods as well as standardized baseline data, measurement unit conversion tools, display of the experiment design analysis in a way which is easily understood, and an optional feedback method for the refinement of the protocol method.

17 Claims, 4 Drawing Sheets

|  | Variable A | Variable B | Variable C | Variable D | |
|---|---|---|---|---|---|
| Experiment 1 | Level 1 | Level 1 | Level 1 | Level 1 | Result 1 |
| Experiment 2 | Level 1 | Level 2 | Level 2 | Level 2 | Result 2 |
| Experiment 3 | Level 1 | Level 3 | Level 3 | Level 3 | Result 3 |
| Experiment 4 | Level 2 | Level 1 | Level 2 | Level 3 | Result 4 |
| Experiment 5 | Level 2 | Level 2 | Level 3 | Level 1 | Result 5 |
| Experiment 6 | Level 2 | Level 3 | Level 1 | Level 2 | Result 6 |
| Experiment 7 | Level 3 | Level 1 | Level 3 | Level 2 | Result 7 |
| Experiment 8 | Level 3 | Level 2 | Level 1 | Level 3 | Result 8 |
| Experiment 9 | Level 3 | Level 3 | Level 2 | Level 1 | Result 9 |

| Variable A | Level 1 | Level 2 | Level 3 | SAVE |
|---|---|---|---|---|
| Variable B | Level 1 | Level 2 | Level 3 | |
| Variable C | Level 1 | Level 2 | Level 3 | |
| Variable D | Level 1 | Level 2 | Level 3 | ? |
| Refine: | Step 2 | Step 3 | Step 4 | Step 5 |

EXPERT SYSTEM UTILIZING A KNOWLEDGE BASE AND DESIGN OF EXPERIMENT (DOE) TECHNIQUES

BACKGROUND FIELD OF THE INVENTION

This invention relates generally to expert systems and more particularly to an expert system for the design of protocols.

BACKGROUND OF THE INVENTION

The statistical methods of multivariable testing, also known as Design of Experiments (DOE), have been used in industrial process design for decades. However, it has not been embraced in the scientific community despite the significant advantages these techniques offer. One notable explanation for this is that DOE methods are perceived as formidably complex.

Scientists commonly design experiments using the traditional one-variable at a time approach. More specifically, all but one variable are held constant while the one under investigation is varied. The test variable is then fixed at some "good" value based on the results and another variable is modified.

This traditional method can be costly in both time and physical resources, particularly in cases where there is a wide variability in assay precision and linearity (a direct relationship) between variables. Additionally the traditional method does not evaluate the interactions among variables.

The statistical methods of DOE are very powerful techniques that can significantly enhance the effectiveness of an experimental design. DOE methods can simultaneously consider interactions between many variables. DOE matrices can reduce the number of test configurations, reduce defects, improve experimental times, reduce expenses, improve the quality of experimental results, and greatly increase the odds of identifying hard-to-find solutions to difficult quality problems. Thus it can be seen that DOE methods are cost effective in both time and physical resources. Further, quality experimental information translates into more reliable decisions and, ultimately, shorter times to product introductions.

Genichi Taguchi carried out significant research with DOE techniques in the late 1940's. His effort has been to make this powerful experimental technique more user friendly and apply it to improve the quality of manufactured products. Most of Taguchi's orthogonal arrays are easier-to-use rearrangements of earlier DOE designs. Interactions can be designed in and analyzed more easily, and the arrays can be modified for mixed-level designs with simple-to-follow steps.

Additionally, classical DOE does not specifically address quality. DOE using the Taguchi approach attempts to improve quality, which is defined as the consistency of performance. The prime motivation behind the Taguchi experiment design technique is to achieve reduced variation, also known as robust design. Robust designs, using ideas derived from Taguchi, allow the user to simultaneously study the controllable factors and reduce the effect of uncontrollable environmental variables. This technique, therefore, is focused on attaining the desired quality objectives in all steps.

Dr. Taguchi's standardized version of DOE, popularly known as the Taguchi method or Taguchi approach, was introduced in the USA in the early 1980's. Because of their simplicity and success in industrial process design, the Taguchi methods offer a cost-effective strategy involving interactions between wide ranging variable combinations. Today it is one of the most attractive quality building tools used by all types of engineers in the manufacturing industries.

The Taguchi philosophy of design of products and/or processes identifies three design stages: systems design, parameter design, and tolerance design. In the first stage, systems design, the designer draws upon his/her knowledge of the process in question to produce an initial design of a product or process. The use of experimentation may be irrelevant during this phase, but will become an essential element at the next stage, parameter design. The objective of parameter design is to choose suitable values for the parameters of the product or process. In the third stage, tolerance design, inexpensive components are replaced by better ones to achieve quality within the desired tolerance.

Current DOE tools assume that the user will have sufficient information to effectively define the first two stages; systems design and parameter design. That is, that the user is familiar with the nuances of the particular plan of the scientific experiment or treatment (protocol method) being employed. They also assume that the user will be able to select appropriate constants, variables, and variable value ranges.

In addition, the user is expected to have a sophisticated knowledge of statistical design and analysis; many programs provide no guidance in the analysis of the results. Often, the user is presented with a lot of statistical output that requires substantial effort to translate results data into relevant answers.

In sum, the use of DOE tools can be complex, daunting, and can require a significant amount of time and effort to master.

These limitations make the use of current DOE design applications unattractive to those who could otherwise make productive use of these powerful statistical design a protocol.

Other inventors have created several types of expert systems for protocol design, employing DOE methods. However, none integrate a combination of a simple user interface, measurement unit conversion tools, specialized learning knowledge bases, a data structure for storing user tested protocol methods, a rule set which is used to process saved data and incorporate it into the knowledge bases, a hierarchy of parameter selection rules, robust experimental design and analysis tools, display the experiment design analysis in a way which is easily understood, and a feedback method for the refinement of the protocol method.

In addition many of these inventions are of such a sophisticated nature that their implementation is limited to hardware and software systems with specialized tools and are thus limited to a small group of users who have access to such facilities. U.S. Pat. No. 4,472,770 (Li, Sep. 18, 1984), U.S. Pat. No. 4,710,864 (Li Dec. 1, 1987) and U.S. Pat. No. 4,910,600 (Li Mar. 20, 1990), "Self-optimizing method and machine", make use of statistical design matrix for automated experiment design and testing an object but assumes that this object is well defined, determines the test designs without human control or interaction, and does not integrate a knowledge base, nor does it have the ability to save results for future reference by others.

Patent JP7200662 (Hiroko, Aug. 04, 1995), "Experiment Plan Production Support Systems Having Design Knowledge Base", requires that the product, the results of a completed process, has already been generated and that the relevant parameters of the initial process that produced the resulting product are known. These results are required before the experiment plan can be generated. In addition, it does not provide for an feedback loop.

U.S. Pat. No. 5,107,499 (Lirov, et al. Apr. 21, 1992), "Arrangement for automated troubleshooting using selective advice and a learning knowledge base", interactively communicates between a user and utilizes a learning knowledge base but it does so in a complex fashion and does not incorporate DOE design methods.

U.S. Pat. No. 5,253,331 (Lorenzen, et al. Oct. 12, 1993), "Expert system for statistical design of experiments", defines a method for interacting with a user to specify an experimental design. However, it does not utilize a knowledge base, nor provide a feedback method after the experiment has been completed, and involves complex interactions between multiple layers of programming language tools and is thus is restrictive in the type of computer hardware and software platforms on which it can be developed.

REFERENCES

"Statistics in Research and Development", Second Edition, Ronald Caulcutt, Chapman & Hall, 1991

Cobb, B. D. and J. M. Clarkson (1994), "A Simple Procedure for Optimizing the Polymerase Chain Reaction (PCR) Using Modified Taguchi Methods," Nucleic Acids Research, Vol. 22, No. 18, pp. 3801–3805.

Briones, P., "Experimental Design: A useful Tool for PCR Optimization", BioTechniques, 21:134–140

"Why Don't More Researchers Use Design of Experiments?", R&D Magazine, January 1995, pp. 31

"DOE Makes Research Pay Off", R&D Magazine, April 1997, pp. 43

SUMMARY

In accordance with the present invention, an expert system is provided which is comprised of a simple user interface, flexible and specialized learning knowledge bases, data structures and process for storing user tested protocol methods, hierarchy of parameter selection rules, measurement unit conversion tools, robust experimental design and analysis tools, display of the experiment design analysis in a way which is easily understood, and an optional feedback method for the refinement of the protocol method.

OBJECTS AND ADVANTAGES

Accordingly, several objects and advantages of the present invention are that it:

Has a simple design for ease of use; it requires the user to complete only a few straightforward selection steps.

Allows the user to store tested protocol design results in a specialized knowledge base which can later be accessed by others.

Allows the user to easily identify standard and previously optimized protocol method constants, variables, and variable ranges by the use of a learning knowledge base. Thus an inexperienced user can efficiently make use of the experience of others which is stored in the knowledge base.

Requires little previous experience with statistics to utilize powerful statistical optimization tools. Thus it creates an opportunity for users who would normally not take advantages of powerful DOE tools because of a lack of the time and/or skills to do so.

Has the flexibility of allowing the user to input and test novel protocol methods, constants, variables, and variable ranges and to add them to the shared knowledge base.

Allows dependent variables with linear (direct) and non-linear relationships to other variables and constants can be quickly and easily identified and the appropriate values determined from the knowledge base.

Allows users to easily refine a protocol method based on previous findings using a feedback selection and repeating the experiment with the best values identified in the analysis step.

Can more easily be implemented on a wide range of current and emerging computer hardware and software systems, unlike other expert systems, because of its simplicity of design.

Other objects and advantages of this invention are that it:

Saves time and labor because it minimizes the amount of effort a user must apply to collect preliminary protocol data, design an experiment, and analyze the results.

Saves time and labor because it enables the user to draw upon work previously completed by others; it reduces duplicated efforts.

Saves time and labor because it minimizes the number of trials necessary to troubleshoot and/or optimize a protocol method.

Satisfies a need for a fast and efficient method of optimizing new and evolving laboratory protocol methods for such quickly growing and competitive industries as biotech, healthcare, and pharmaceuticals.

Takes into account the wide variation of measurement unit standards in many fields of science by incorporating convenient measurement unit conversion tools for experimental constant and variable range units to standard and non-standard values.

Has the flexibility to incorporate knowledge bases of varied structure for efficient management of a broad range of protocol data.

Further objects and advantages of this invention will become apparent from a consideration of the drawings and the ensuing description

DRAWING FIGURES

FIG. 2 is a generalized series of selection/input screen elements for steps a

REFERENCE NUMERALS IN DRAWINGS

11 Step a-1: selection/input of a protocol and protocol method.
12 Step a-2: selection/input of constants.
13 Step a-3: selection of DOE matrix design and/or number of variables and variable value levels to be tested.
14 Step a-4: selection/input of variables.
15 Step a-5: selection/input of variable ranges.
16 Step b: Generation and display of experiments and results input screen elements.

17 Step e: Identification of optimal values, troubleshooting, data storage, and step refinement options.
50 Structures: Protocols data
52 Structures: Methods data
54 Structures: Constants data
56 Structures: DOE matrix design data
58 Structures: Variables data
60 Structures: Variable range data
62 Process: Results data input and Analysis of test results
64 Structures: Saved user tested methods data
66 Process: Analysis of collected user methods data
68 Structures: Troubleshooting data
70 Structures: Parameter relationships where parameters include all factors in a protocol

CONCLUSION, RAMIFICATIONS, AND SCOPE OF INVENTION

This invention provides the user with a unique tool which has the advantages of a simple user interface, flexible and specialized learning knowledge bases, data structure and process for storing user tested protocol methods, hierarchy of parameter selection rules, measurement unit conversion tools, robust experimental design and analysis tools, display of the experiment design analysis in a way which is easily understood, and an optional feedback method for the refinement of the protocol method.

There are many novel and emerging protocol methods whose development could be significantly enhanced by the current invention. An example is the polymerase chain reaction (PCR). An important emerging biological protocol, PCR is a technique that is used to make many copies of a specific region of DNA. This is done to produce enough copies so that the DNA can be adequately tested. It has a rapidly growing range of uses in such areas as assessment of therapy effectiveness, the detection of infectious microorganisms, genome mapping, quality testing, basic molecular biology research, and many other significant applications. PCR has a wide variability in assay (analysis of one or more components) precision and linearity between the various methods and standards; as with any new technique, there are a wide range of standards used by scientists and described in the literature. In addition, because PCR is a relatively new protocol, a large number of people using it have a limited knowledge of PCR methods. The current invention addresses these issues.

More generally this application can be applied to such areas as medicine. For example, in the design of treatments which involve complex drug and therapeutic combinations and interactions. In business and marketing, professionals could use this tool to improve their products and services by determining what feature combinations are most needed and desired by consumers. It could be used to define effective rules and policies by helping to define what combination of factors influence a particular outcome in social environments.

We are in an era where data and information are accumulating at an accelerating rate. The explosive power of the Internet, which this invention is designed to utilize, is a notable example. To effectively and efficiently take advantage of this growing base of information, there is a need for tools such as this invention. These tools simplify the analysis of complex combinations of information and determine the significant factors so that effective and reliable decisions can be made.

The potential for an invention such as this is enormous. Because of its relatively simple design, relevant information can be identified and utilized with substantially more ease and convenience than before. Because of the powerful statistical tools that it incorporates, information can be uncovered that was previously unknown about the interactions between variable element combinations. People who would otherwise be limited in the scope of their contributions to the advancement of research and analysis of trends can participate more fully in the discovery of this knowledge.

While the above description contains many specifics these should not be construed as limitations on the scope of the invention, but rather as an exemplification of one preferred embodiment thereof. Many other variations are possible.

Accordingly, the scope of the invention should be determined not by the embodiments illustrated, but by the appended claims and their legal equivalents.

DESCRIPTION FIGS. 1–5

Figure 1:
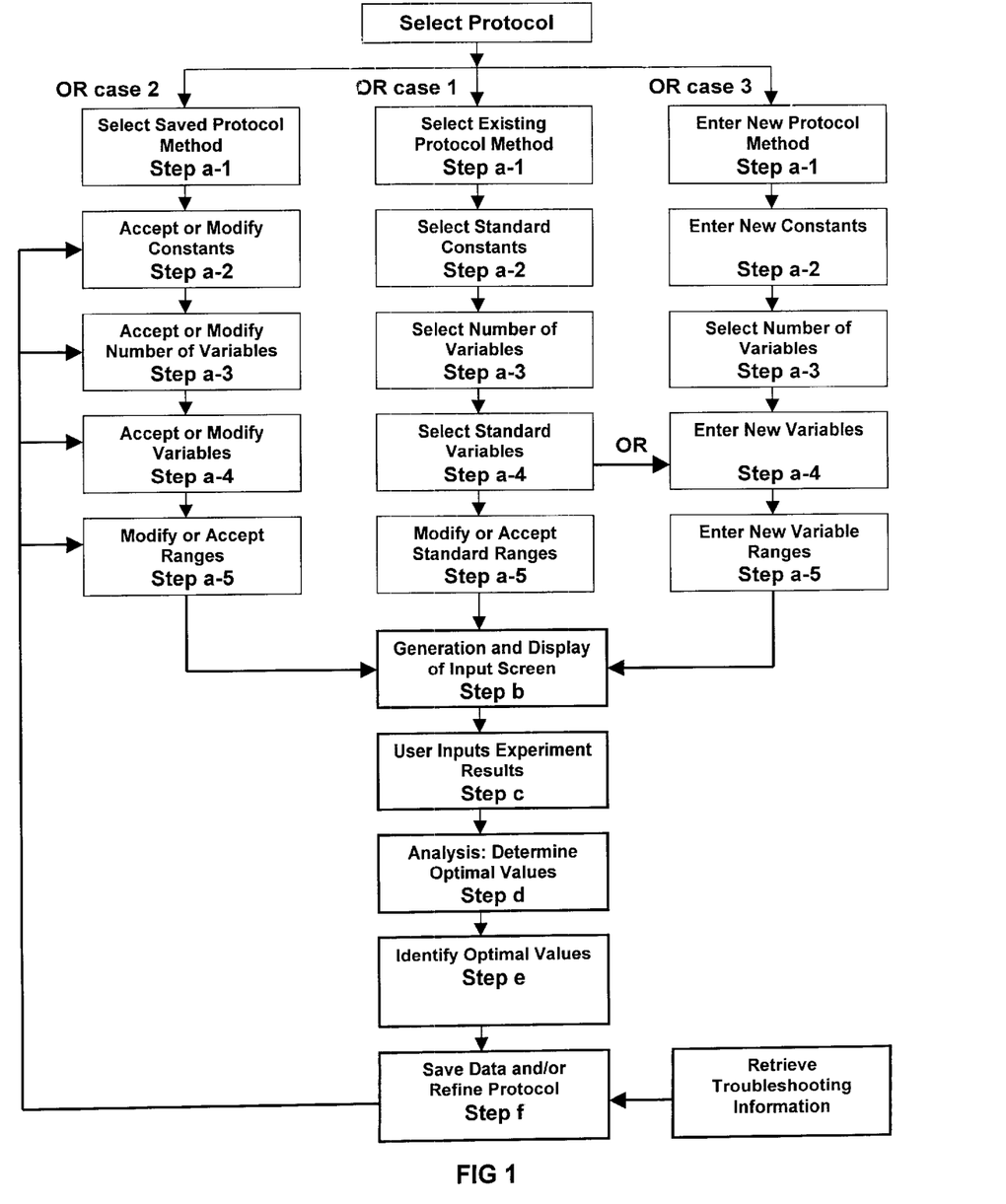
FIG. 1 is a generalized flow chart of the present invention.

Description of FIG. 1

A generalized flow chart of the present invention is illustrated in FIG. 1. The user begins by selecting one of three options to define his/her experiment design parameters:

case 1: with the guidance of the knowledge base and help contents case 2: by modifying a previously designed, tested, and retrieved protocol method case 3: by inputting entirely new protocol method data.

A typical embodiment of the method of the present invention begins at step a-1. In case 1 the user selects from a list of currently defined protocol methods available in the database; in case 2 the user makes no changes; in case 3 the user inputs the name of the new protocol method to be tested.

For step a-2 the user identifies the constants that are specific to the method selected in step a-1. In case 1 constant selections are retrieved from the knowledge base; in case 2 the user either accepts or modifies existing constants; in case 3 the user inputs the appropriate constants.

Next in step a-3, the user selects the number of variables to be tested. This selection determines the design matrix that will be used in generating the experiment design. In the preferred embodiment the robust design matrixes of Taguchi are used. In case 1 the user selects from the knowledge base options; in case 2 the user either accepts or modifies the existing number of variables; in case 3 the user selects from the DOE method options.

In step a-4 the user identifies the variables specific to the method identified in step a-1, to the constants identified in step a-2, and the number of variables which have been determined in step a-3. In case 1 variable selections are retrieved from the knowledge base; in case 2 the user either accepts or modifies existing variables; in case 3 the user inputs the appropriate variables.

In step a-5 the user identifies variable range values specific to the method identified in step a-1, to the constants identified in step a-2, the number of which have been determined in step a-3, and specific to the variables selected in step a-4. In case 1 variable range selections are retrieved from the knowledge base. These selections can either be standard protocol method values or determined by functions based on the relationships between the variables and constants identified in the preceding selections; in case 2 the user either accepts or modifies existing variable ranges; in case 3 the user inputs the appropriate variable ranges.

After the parameter selection just described, all of the three cases noted above now follow the same series of steps.

In accordance with the input of the data identified in steps a-1 through a-5, an experiment design is generated in step b.

The user now inputs the results of the experiment design in step c. Alternately, the results data can be retrieved from an automated system which controls the experiment tests and/or measures the test results.

The next action is the analysis of the data input in step c. For the Taguchi method in the preferred embodiment, the function used in step d is the signal to noise ratio or SNT:

$$SNT = -10 \log[(SD/mean)^2]$$

Where SD is the standard deviation. The mean is a middle point between extremes; that is, the expected value.

In step e, the optimal combination of variable values for this experimental design is identified and displayed for the user. In the preferred embodiment, a display of experimental variables and their respective range values are displayed with the best combinations highlighted so that the user can easily interpret the results.

Finally, in step f the user can save the experiment and the test results to the knowledge base. This data is saved so that it can later be retrieved for use by others and/or additional refinement. In addition, the protocol method parameters and related test results can be processed and incorporated into the standardized knowledge base as appropriate.

The user may now return to any of the previous steps to refine his/her experiment protocol based on the information gathered in the preceding process. In the preferred embodiment if the user returns to step a-5, the selection of variable ranges, the best values identified in step e are now the proffered mid-range values. The higher and lower values can either be determined by a set of standard default ranges or by formulas which define known linearities between interrelated constants and variables. These ranges and formulas will be unique to the protocol method, constants, and/or variables involved.

Because of the wide range of protocols, each with its own unique components and component relationships, there are various possibilities with regards to the specific interface designs for step a, the definition of experiment parameters.

Figure 4:
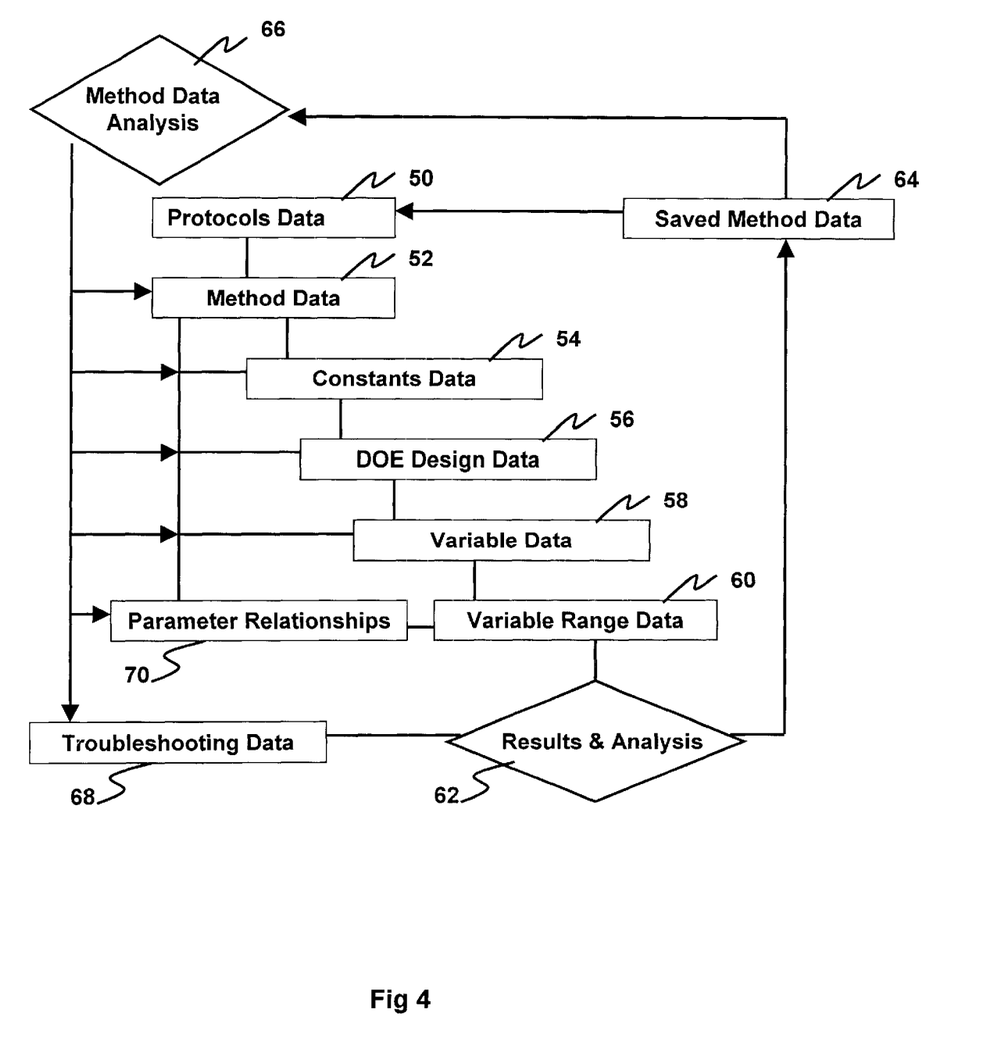
FIG. 4 is a generalized flow chart of the relationships among the knowledge base data.

Knowledge base schemas will vary for this reason as well. More specifically, the relational database designs, which are composed of individual structures containing protocol methods, constants, variables, variable ranges, parameter relationships, and troubleshooting data will depend on the protocols being addressed. A generalized database schema is illustrated in FIG. 4.

Figure 2:
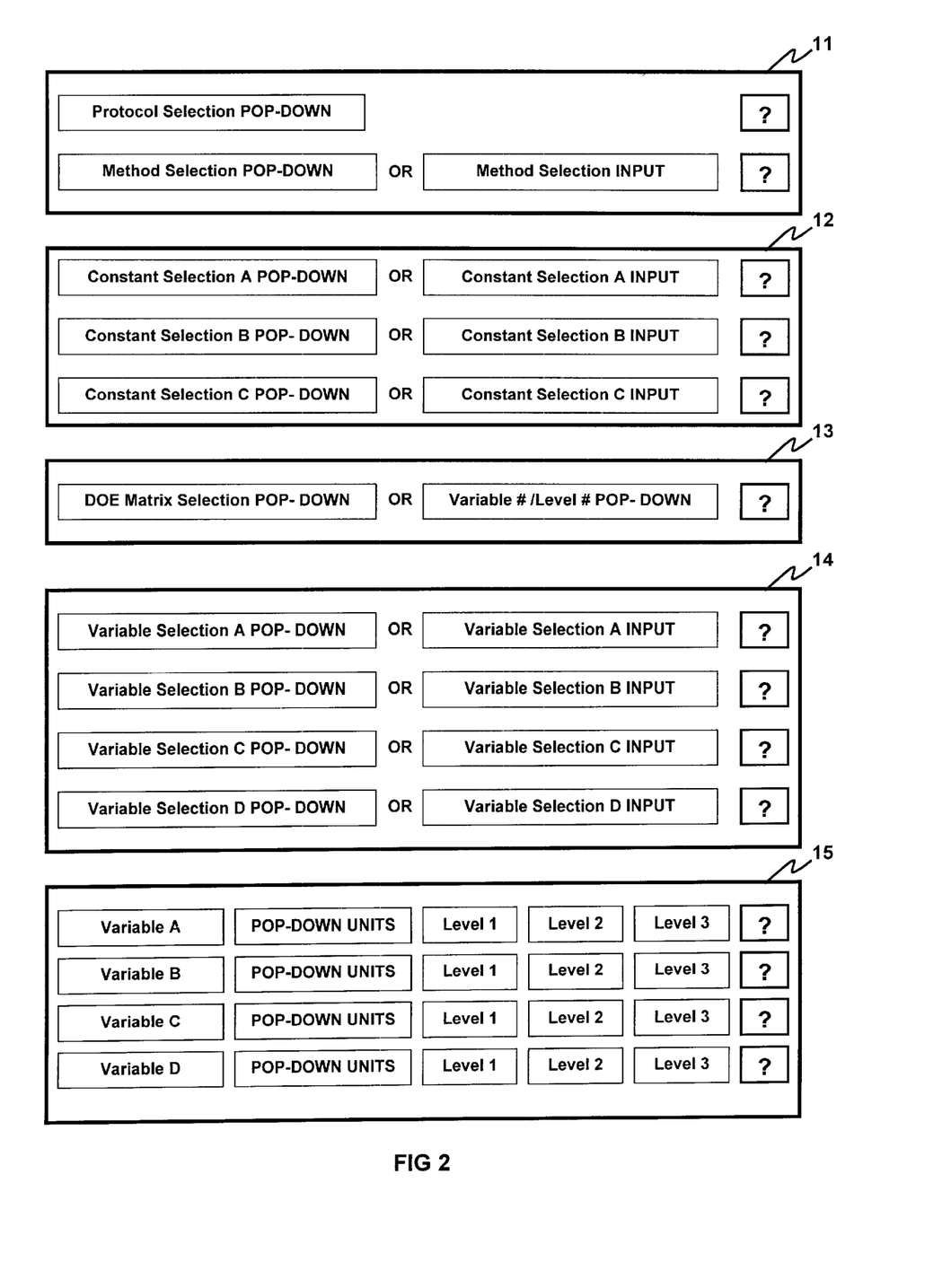

Description of FIG. 2

Figure 3:
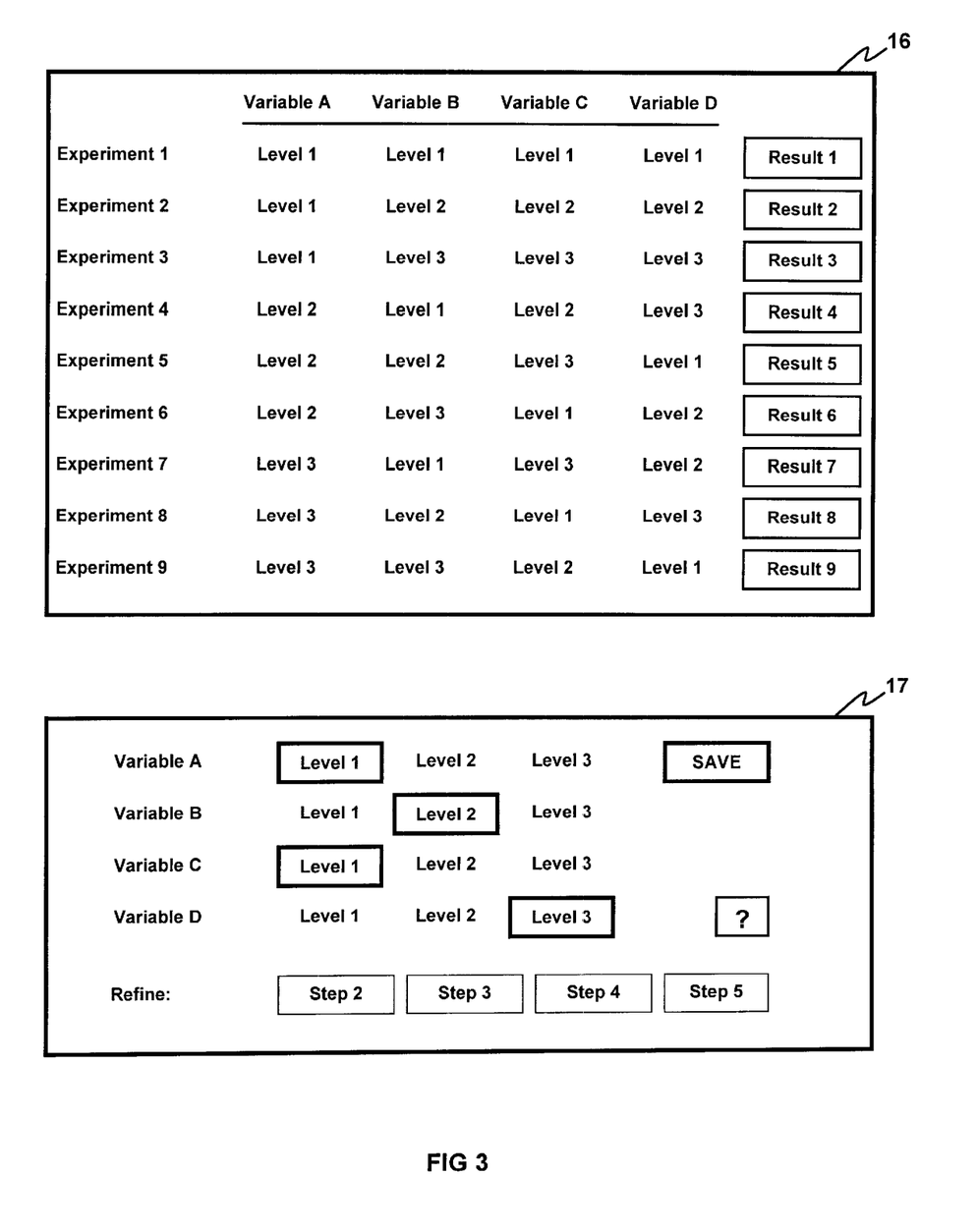
FIG. 3 is a generalized series of selection/input screen elements for steps b through f.

A generalized illustration of selection/input and display screen elements are presented in FIGS. 2 and 3. In the preferred implementation, the knowledge base data is stored on servers which can be accessed over a LAN (Local Area Network), WAN (Wide Area Network), or the Internet. In this way many people can easily and conveniently share knowledge base data. In all of the illustrations, the boxes with a "?" indicate a help button. The help buttons allow the user access to relevant parameter detail information in the knowledge base.

On the left-hand side of each of the step a selection/input screen elements in FIG. 2 there is a selection pop-down box. These are the selections determined by the knowledge base and applied in case 1 and case 2 discussed and identified in FIG. 1. On the right hand side of the selection/input screens there are boxes which identify input boxes. These are for case 3 in which the user inputs new information which is not present in the knowledge base.

The following description will use PCR as a sample protocol to help describe how the illustrated input screens can relate to one another. The following will be case 1, a new experiment design which is made with selections from the knowledge base.

In step a-1 (2(a)) the user selects a protocol, PCR, and a method. The method selections are determined by the protocol selection. Because there may be many methods, each with it's own advantages and disadvantages, the user can optionally review the necessary method information retrieved from the knowledge base by clicking on the help button. In this example the PCR protocol method selected will be in situ PCR, a knowledge base selection from the pop-down menu.

The method selected will determine which set of constants the user selects from in step a-2 (2(b)): In this case the constants would be polymerases, enzymes which catalyze the formation of DNA, and primer pairs, short sequences of DNA which bind to the ends of the sequence to be copied. The selection of these constants are guided by information provided to the user from the knowledge base by clicking on the help button.

These selected constants will later influence the variables and variable ranges suggested to the user.

The number of variables to be tested are determined next in step a-3 (2(c)): In this example, the Taguchi method is selected and the user identifies that he/she wants to test four variables at three levels (min, mid, and max variable value levels). The Taguchi method uses specific matrix sizes which will determine the number of tests to be run. For this reason, the number of variables identified by the user determines the experimental design matrix used. Alternately, the matrix design selected will determine the number of variables and variable values to be tested. The user is guided in this selection by information which can be retrieved from the knowledge base by clicking on the help button.

Based on the PCR method and constants selected, the user is presented with a set of variables to choose from in step am (2(d)). The number of variables the user can select from are those he/she identified in step a-3 (2(c)). In this case, the user will select four variables. The user is guided in this selection by information which can be retrieved from the knowledge base by clicking on the help button. Alternately the user can enter the name/id of other variables he/she would like to test which are not currently in the knowledge base.

If in the aforementioned steps the user has selected values that exist in the knowledge base, variable value levels will be suggested to be accepted or modified in step a-5 (2(e)). In this example, the suggested variable value levels for each of the four selected variables will appear in the boxes labeled "Level 1", "Level 2", and "Level 3".

For example, if the protocol method chosen is in situ PCR, the variable Mg++ has a standard range of 1.5–5.0 mM. However, if the polymerase constant chosen is the polymerase UITma, the suggested Mg++ range will be limited to 1.5–2.0 mM. Thus the three boxes would display "1.5 mM", "1.75 mM", and "2.0 mM" respectively.

Similarly, the standard melting temperature range is 68° C.–75° C. However, the suggested temperature ranges will be determined with a formula which uses the characteristics of the primer pair constants: 62.3° C.+0.41° C. (%G-C)– 500/(primer length).

In either case, the user can utilize a unit conversion tool so that the units are most convenient for the user. An example would be if the user prefers to use mg/L instead of mM. By changing the pop-down selection from the default measurement units of mM to mg/L, the values in the three boxes would be converted to the appropriate values for the selected unit.

The suggested values in these boxes can also be modified by the user as needed.

If the variable is not currently identified in the knowledge base, the user will enter the ranges known by him/her to be reasonable in this step.

Description of FIG. 3

Now that the user has made the necessary parameter selections in step a, the experiment design and the input screen elements for experiment results in step b (2(*a*)) are generated. In step c the user inputs the results of the experiments described in the table. In this example the set of nine experiments displayed are those of a Taguchi matrix for four variables and three range levels.

After the analysis of these results are completed in step d, the optimal combination of experimental variable values are identified in a clear and simple manner to the user in step e (2(*b*)). In this example, the best variable levels are identified by the bold boxes.

The user can now get troubleshooting information by clicking on the help button. If, for example, the user has low specificity in his/her PCR reaction, he/she can identify possible causes and solutions from the information retrieved from the knowledge base.

In step f the user can click on the "SAVE" button to save the data from the completed process to the knowledge base for future reference. This data can also be processed along with other saved protocol method test results to determine linear and non-linear relationships between parameters and incorporated into the knowledge base data used for the initial design of protocols.

If further refinement of the protocol method is desired, the user can return to any of the previous steps. If the user returns to step a (2(*e*)) directly from step f (2(*b*)), the optimal values determined in the just completed series of steps will be the new mid-range values. In this example the best variable value levels indicated with bold boarders in the analysis screen (2(*b*)) will appear in the boxes labeled "Level 2". New higher and lower variable range values can be estimated from previously defined rules from the knowledge base and accepted or modified by the user. These rules will be unique to the protocol method, constants, and/or variables involved.

Description of FIG. 4

Introduction: This figure is a generalized knowledge base schema to help illustrate the preferred embodiment discussed. The data structures can include, for example, database tables or data arrays. Any of the data types identified by the boxes in the figure can consist of a number of related data structures. In this way, data of the same type, such as constant data (54), with unique characteristics can be stored and retrieved more efficiently.

The parameter relationship structures (70) identify the known optimal range values for data combinations. It could be static maximum and minimum values or it could be a formula based on a data element combination such as a selected method and a variable. For example if the data pair is the method in situ PCR and the variable Mg++ the known optimal variable range for Mg++ would be identified as the static values 1.5 mM to 5.0 mM.

Similarly for the case where the data pair is the constant primers and the variable temperature. The relationship will be defined by a formula based on the characteristics of the selected primer pair: 62.3° C.+0.41° C. (%G-C)−500/ (primer length) will be the suggested melting temperature. Note that in some cases, there can be relationships between more than two parameters, such as two variables and a constant, which this set of parameter relationship data can identify. This is illustrated in the case of two variables Mg++ and dNTP and the constant polymerase UITma. To determine the best variable range for dNTP the relationship information indicates that Mg++ ions should exceed that of total dNTP concentration by 0.5 mM–3.0 mM. As identified above, the Mg++ level for UITma is best between 1.5–2.0 mM. Thus, the suggested range of dNTP, 2.0–5 mM, is determined by considering its combination with another variable and a constant.

Schema Description: The process begins by the selection from the protocols data (50) followed by a selection from the protocol methods data (52). In the example this would be the protocol PCR and the method in situ.

The possible and/or required constants used in this method are identified from the constants data (54). In the example, the constant types identified from the data structure would be polymerases and primer sets.

The constant elements of polymerases and primer sets identified are also chosen from this set (54); UITma and a primer set AB. As noted above, there can be more than one data structure in a data type set. In this example the polymerase and primer set selections and related information are contained in separate but similarly defined data structures to facilitate efficient data storage and retrieval.

For the purposes of illustrating the preferred embodiment, the DOE matrix selection takes place next. This selection determines how many variables are selected in the next step. Alternately, the selection of the number of variables and range levels the user wishes to test will determine which DOE matrix is used for the design and analysis of the experiment.

The appropriate number and type of variable data (58) are now selected. These selections are determined by the previously selected parameters and the parameter relationship sets (70). For example, the variables presented for selection will be dependent on the method chosen and possibly the constant selections. In addition, the number of variables that can be selected are limited to the number identified in the matrix selection set.

For consistency with FIG. 1, variable range data (60) is represented separately from the variable data structure (58) in this schema. Variable ranges are determined by referring to the parameter relationship data (70) that identify relationships between parameters such as the selected method, constants, and other variables.

After the experiment test results have been entered, it is analyzed (62). Here, if required, the troubleshooting data structure (68) is referred to as appropriate. The completed method experiment design, results, and analysis can now be stored in the saved method data structure (64).

The saved method data structure (64) can be in any number of formats, depending on the size of the data set and software/hardware platform being used. In the preferred embodiment it is stored in a flat file, such as a browser cookie. For larger and more complex protocol methods it may have any number of embodiments.

This saved method data (64) can be added to the knowledge base after being processed though the method data analysis (66). This analysis consists of a set of rules that determine the appropriate storage in any of the knowledge base data structures mentioned above.

What is claimed is:

1. A method of teaching protocol design, the method comprising a user Interface, hierarchy of parameter selection rules, knowledge bases, statistical design and analysis tools, and data structures and processing for storing said protocols, further comprising the steps of:
 a) inputting information to a computer with a user interface selected from the group comprising the aspects of a computer system or program which can be seen, heard, or otherwise perceived by the user, and the commands and mechanisms the user employs to control Its operation and input data;
 b) inputting to the computer parameters selected from the group consisting of data obtained from user interface input data selected from a knowledge base comprising a plurality of protocol data, end experimental designs selected from the group consisting of a plurality of DOE methods and robust design methods;
 c) generating and communicating a design in a accordance with said parameters selected in step b;
 d) inputting information to the computer, the information including results performed in accordance with the design generated in step c;
 e) analyzing the results utilizing data contained in said knowledge base;
 f) communicating the evaluation, said evaluation selected from the group comprised of the design, the results data, results data analysis of step e, and said knowledge base;
 g) communicating an option for the user to return to any of the previous steps for further design modifications;
  whereby one with or without skill in the art to which a protocol pertains, can successfully learn a protocol design.

2. The method of claim 1 wherein any parameter selection is accompanied by a resource for converting protocol data measurement units to measurement units selected from the group consisting of all measurement units.

3. The method of claim 1 wherein said parameters selections are evaluated prior to the generation of the design.

4. The method of claim 1 wherein said knowledge base includes data processed by a rule set applied to date selected from the group consisting of completed protocol designs, results, and results analysis.

5. The method of claim 1 wherein said knowledge base consists of scientific protocols in biological sciences.

6. The method of claim 1 wherein said knowledge base consists of biological sciences relating to genomica.

7. The method of claim 1 wherein said knowledge base consists or marketing protocols.

8. The method of claim 1 wherein said knowledge base consists of marketing protocols relating to the Internet.

9. The method of claim 1 wherein the resulted analysis include identification of optimal parameter combination.

10. The method of claim 1 wherein the invention components are distributed among more that one neworked compuler.

11. A machine for the teaching of protocol design said machine comprising a user interface hierarchy of parameter selection rules, knowledge bases, statistical design and analysis tools, and data structures and processing for storing said protocols, further comprising the steps of:
 means for inputting Information to a computer with a user interface selected from the group comprising the aspects of a computer system or program which can be seen, heard, or otherwise perceived by the user, and the commands and mechanisms the user employs to control its operation and Input data;
 means for inputting to the computer parameters selected from the group consisting of data obtained from user interface input, data selected from a knowledge base comprising a plurality of protocol data and experimental designs selected from the group consisting of a plurality of DOE methods and robust design methods:
  means for generating and displaying a protocol design in accordance with said designs and said knowledge base;
  means for inputting result data to the computer;
  means for evaluating the results data;
  means for communicating the evaluation, said evaluation selected from the group comprised of the design, the results data, results data analysis and said knowledge base;
  means for saving the design arid the results for retrieval, evaluation, and incorporation into said knowledge base;
  means for a user to return to any of the previous machine process elements;
   whereby one with or without skill in the arts to which a protocol pertains, can successfully learn a protocol.

12. The machine of claim 11 wherein any parameter selection is accompanied by a resource for converting protocol data measurement units to measurement units selected from the group consisting of all measurement units.

13. The machine of claim 11 wherein said parameters selections are evaluated prior to the generation of the protocol design.

14. The machine of claim 11 wherein said knowledge base includes data processed by a rule set applied to data selected from the group consisting of completed protocol designs, results, and results analysis.

15. The machine of claim 11 wherein said knowledge base consists of scientific protocols in biological sciences.

16. The machine of claim 15 wherein said knowledge base consists of biological sciences relating to genomics.

17. The machine of claim 11 wherein invention components are distributed among more than one neworked computer.

* * * * *